(12) United States Patent
Ozaki et al.

(10) Patent No.: US 6,238,896 B1
(45) Date of Patent: May 29, 2001

(54) PROCESS FOR PRODUCING MALONIC ACID DERIVATIVES

(75) Inventors: Eiji Ozaki; Kanehiko Enomoto, both of Hiroshima; Takakazu Endo, Kanagawa, all of (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 0 days.

(21) Appl. No.: 09/367,716

(22) PCT Filed: Feb. 20, 1998

(86) PCT No.: PCT/JP98/00711

§ 371 Date: Aug. 20, 1999

§ 102(e) Date: Aug. 20, 1999

(87) PCT Pub. No.: WO98/37219

PCT Pub. Date: Aug. 27, 1998

(30) Foreign Application Priority Data

Feb. 20, 1997 (JP) .................................................. 9-036508
Feb. 20, 1997 (JP) .................................................. 9-036510

(51) Int. Cl.$^7$ ........................................................ C12P 7/62
(52) U.S. Cl. .......................... 435/135; 435/170; 435/822; 435/843

(58) Field of Search ...................................... 435/135, 843, 435/822, 170

(56) References Cited

FOREIGN PATENT DOCUMENTS 7-99983 * 4/1995 (JP) .

* cited by examiner

*Primary Examiner*—Herbert J. Lilling
(74) *Attorney, Agent, or Firm*—Oblon, Spivak, McClelland Maier & Neustadt, P.C.

(57) ABSTRACT

The present invention relates to a method for preparing a malonic acid monoester represented by Formula (II):

HOOCCH$_2$COOR            (II)

wherein R is alkenyl, aryl, aralkyl or C$_{1\text{-}20}$ alkyl, comprising treating a cyanoacetic acid ester represented by Formula (I):

NCCH$_2$COOR            (I)

wherein R is defined in Formula (II), with a culture, cells or a product from treated cells of a microorganism belonging to the genus Corynebacterium, Gordona or Rhodococcus and having nitrilase activity to thereby hydrolyze the cyanoacetic acid ester.

11 Claims, No Drawings

PROCESS FOR PRODUCING MALONIC ACID DERIVATIVES

This application is a 371 of PCT/JP98/00711 filed Feb. 20, 1998.

TECHNICAL FIELD

The present invention relates to a method for preparing malonic acid monoesters which are useful as intermediates in the synthesis of various chemical products, medicines, agricultural chemicals and so on.

BACKGROUND ART

As a method for preparing malonic acid monoesters, chemical hydrolysis of malonic acid diesters is commonly used. According to this method, however, it is difficult to separate the generated malonic acid monoester from the unreacted malonic acid diester and the malonic acid which is a by-product. Thus, it is impossible to obtain highly pure malonic acid monoesters.

As a method for obtaining highly pure malonic acid monoesters, a method using Meldrum's acid as a raw material is known [see, for example, Matoba Katsuhide et al., Chem. Pharm. Bull., 31 (8), 2955 (1983); or Rigo B. et al., Tetrahedron Lett., 30(23), 3073 (1989)]. However, since this method uses expensive Meldrum's acid, it cannot be said a practical method and is not suitable for industrial production.

As another method for obtaining highly pure malonic acid monoesters, a method is known in which malonic acid diesters are treated with an enzyme or microorganism having an ability to hydrolyze ester bonds (Japanese Unexamined Patent Publication No. 8-173174). However, the use of malonic acid diesters as a raw material is disadvantageous in terms of cost.

Therefore, development of a highly productive method for preparing highly pure malonic acid monoesters has been desired.

DISCLOSURE OF THE INVENTION

It is the object of the present invention to provide a highly productive method for preparing malonic acid monoesters which are useful as intermediates in the synthesis of various chemical products, medicines, agricultural chemicals, etc.

The present inventors have found that a malonic acid monoester is produced selectively when a cyanoacetic acid ester is treated with a culture, cells or a product from treated cells of a microorganism having nitrilase activity; according to that method, a highly pure malonic acid monoester can be prepared without side reactions such as hydrolysis of ester bonds. Thus, the present invention has been achieved.

The present invention includes the following inventions.

(1) A method for preparing a malonic acid monoester represented by Formula (II):

$$\text{HOOCCH}_2\text{COOR} \qquad (II)$$

wherein R is alkenyl, aryl, aralkyl or $C_{1-20}$ alkyl, comprising treating a cyanoacetic acid ester represented by Formula (I):

$$\text{NCCH}_2\text{COOR} \qquad (I)$$

wherein R is as defined in Formula (II), with a culture, cells or a product from treated cells of a microorganism belonging to the genus Corynebacterium, Gordona or Rhodococcus and having nitrilase activity to thereby hydrolyze the cyanoacetic acid ester.

(2) The method of (1) above, wherein the cyanoacetic acid ester is continuously added to the reaction solution while maintaining the concentration of the cyanoacetic acid ester in the solution in the range from 0.01 to 10% by weight during the hydrolysis.

(3) The method of (1) above, wherein the $C_{1-20}$ alkyl represented by R is $C_{3-20}$ alkyl and the microorganism having nitrilase activity is a microorganism belonging to the genus Rhodococcus.

(4) The method of (3) above, wherein the cyanoacetic acid ester is continuously added to the reaction solution while maintaining the concentration of the cyanoacetic acid ester in the solution in the range from 0.01 to 10% by weight during the hydrolysis.

(5) The method of (1) above, wherein the microorganism having nitrilase activity is *Corynebacterium nitrilophilus* ATCC 21419.

(6) The method of (1) above, wherein the microorganism having nitrilase activity is *Gordona terrae* MA-1 (FERM BP-4535).

(7) The method of (1) above, wherein the microorganism having nitrilase activity is *Rhodococcus rhodochrous* ATCC 33025.

(8) A method for preparing a malonic acid monoester represented by Formula (II'):

$$\text{HOOCCH}_2\text{COOR'} \qquad (II')$$

wherein R' is alkenyl, aryl, aralkyl or $C_{3-20}$ alkyl, comprising treating a cyanoacetic acid ester represented by Formula (I'):

$$\text{NCCH}_2\text{COOR'} \qquad (I')$$

wherein R' is as defined in Formula (II'), with a culture, cells or a product from treated cells of a microorganism having nitrilase activity to thereby hydrolyze the cyanoacetic acid ester.

(9) The method of (8) above, wherein the cyanoacetic acid ester is continuously added to the reaction solution while maintaining the concentration of the cyanoacetic acid ester in the solution in the range from 0.01 to 10% by weight during the hydrolysis.

Hereinbelow, the present invention will be described in detail.

The alkyl represented by R in Formula (I) or (II) may be of either a straight-chain or branched-chain structure. The number of carbon atoms in this alkyl is 1–20, preferably 1–10 and more preferably 2–6. Specific examples of this alkyl include methyl, ethyl, n-propyl, isopropyl, n-butyl, sec-butyl, tert-butyl, isobutyl, n-pentyl, isopentyl, hexyl, heptyl, octyl, 2-ethylhexyl, decyl, dodecyl, tetradecyl, hexadecyl, octadecyl and eicosyl.

The alkyl represented by R' in Formula (I') or (II') may be of either a straight-chain or branched-chain structure. The number of carbon atoms in this alkyl is 3–20, preferably 3–10 and more preferably 3–6. Specific examples of this alkyl include n-propyl, isopropyl, n-butyl, sec-butyl, tert-butyl, isobutyl, n-pentyl, isopentyl, hexyl, heptyl, octyl, 2-ethylhexyl, decyl, dodecyl, tetradecyl, hexadecyl, octadecyl and eicosyl.

The alkenyl represented by R may be of either a straight-chain or branched-chain structure. The number of carbon atoms in this alkenyl is 2–20, preferably 2–6. Specific examples of this alkenyl include vinyl, allyl, crotyl (2-butenyl) and isopropenyl (1-methylvinyl).

The alkenyl represented by R' may be of either a straight-chain or branched-chain structure. The number of carbon atoms in this alkenyl is 3–20, preferably 3–6. Specific examples of this alkenyl include allyl, crotyl (2-butenyl) and isopropenyl (1-methylvinyl).

As the aryl represented by R or R', an aromatic hydrocarbon group such as phenyl, 1-naphthyl, 2-naphthyl; an aromatic hetrocyclic group such as furyl, thienyl, pyrrolyl, oxazolyl, isoxazolyl, thiazolyl, isothiazolyl, imidazolyl, pyrazolyl, pyridyl, pyrimidinyl, pyridazinyl, pyrazinyl, quinolyl, isoquinolyl; or the like may be enumerated.

As the aralkyl represented by R or R', benzyl, 1-naphthylmethyl, 2-naphthylmethyl, phenethyl (2-phenylethyl), 1-phenylethyl, phenylpropyl, phenylbutyl, phenylpentyl, phenylhexyl, methylbenzyl, methylphenethyl, dimethylbenzyl, dimethylphenethyl, trimethylbenzyl, ethylbenzyl, diethylbenzyl or the like may be enumerated.

Among the cyanoacetic acid esters represented by Formula (I), representative compounds are, for example, methyl cyanoacetate, ethyl cyanoacetate, n-propyl cyanoacetate, isopropyl cyanoacetate, n-butyl cyanoacetate, tert-butyl cyanoacetate, 2-ethylhexyl cyanoacetate, allyl cyanoacetate and benzyl cyanoacetate.

Among the cyanoacetic acid esters represented by Formula (I'), representative compounds are, for example, n-propyl cyanoacetate, isopropyl cyanoacetate, n-butyl cyanoacetate, tert-butyl cyanoacetate, 2-ethylhexyl cyanoacetate, allyl cyanoacetate and benzyl cyanoacetate.

The microorganism to be used in the invention is not particularly limited as long as it belongs to the genus Corynebacterium, Gordona or Rhodococcus and has nitrilase activity. Specific examples of the microorganism include *Corynebacterium nitrilophilus* ATCC 21419, *Gordona terrae* MA-1 (FERM BP-4535) and *Rhodococcus rhodochrous* ATCC 33025.

Among these microorganisms, *Gordona terrae* MA-1 has been deposited at the National Institute of Bioscience and Human-Technology, Agency of Industrial Science and Technology, 1–3, Higashi 1-chome, Tsukuba-shi, Ibaraki-ken, Japan, under the above-indicated accession number. *Corynebacterium nitrilophilus* and *Rhodococcus rhodochrous* are available from depositories such as American Type Culture Collection (ATCC), 12301 Parklawn Drive, Rockville, Md. 20852, U.S.A.

When a cyanoacetic acid ester represented by Formula (I) wherein R is alkenyl, aryl, aralkyl or $C_{3-20}$ alkyl [i.e. a cyanoacetic acid ester represented by Formula (I')] is used as the substrate, the microorganism to be used is not particularly limited as long as it has nitrilase activity. In addition to the above-described microorganisms, a microorganism belonging to the genus Pseudomonas, Brevibacterium, Nocardia, Arthrobacter, Bacillus, Escherichia, Micrococcus, Streptomyces, Aeromonas, Mycoplana, Cellulomonas, Erwinia or Candida, for example, and having nitrilase activity may be used in the invention.

More specifically, *Pseudomonas synxanta* IAM 12356, *Brevibacterium acetylicum* IAM 1790, *Nocardia asteroides* IFO 3384, *Arthrobacter oxydans* IFO 12138, *Bacillus subtilis* ATCC 21697, *Escherichia coli* IFO 3301, *Micrococcus luteus* ATCC 383, *Streptomyces griseus* IFO 3355, *Aeromonas punctata* IFO 13288, *Mycoplana dimorpha* ATCC 4297, *Cellulomonas fimi* IAM 12107, *Erwinia herbicola* IFO 12686 or *Candida guilliermondii* IFO 0566 may be enumerated. Of these, microorganisms with ATCC numbers are available from American Type Culture Collection, 12301 Parklawn Drive, Rockville, Md. 20852, U.S.A.; those with IAM numbers are available from IAM Culture Collection, Center for Cellular and Molecular Research, Institute of Molecular and Cellular Biosciences, The University of Tokyo, 1-1, Yayoi 1-chome, Bunkyo-ku, Tokyo, Japan; and those with IFO numbers are available from Institute for Fermentation, Osaka, 17–85, Jusohonmachi 2-chome, Yodogawa-ku, Osaka-shi, Osaka, Japan.

The microorganism may be cultured in either a liquid medium or solid medium. A medium is used which appropriately contains carbon sources and nitrogen sources usually assimilable to microorganisms, vitamins, minerals, and the like. It is also possible to add to the medium a small amount of a nitrile or lactam compound in order to improve the hydrolyzing ability of the microorganism. The nitrile compound is a $C_{1-12}$ straight-chain or branched-chain aliphatic or aromatic nitrile. For example, propionitrile, isovaleronitrile, hexanenitrile, acrylonitrile, adiponitrile, benzonitrile, 2-pyridinecarbonitrile or the like may be enumerated. As the lactam compound, γ-butyrolactam, δ-valerolactam or ε-caprolactam may be enumerated, for example. The cultivation is carried out at a temperature and a pH level at which the microorganism can grow. Preferably, the cultivation is carried out under the optimum cultivation conditions for the microorganism strain used. In order to promote the growth of the microorganism, aeration-agitation may be employed.

In the present invention, a culture obtained by culturing the above-mentioned microorganism with nitrilase activity in a medium may be used without any treatment. Alternatively, cells of the microorganism harvested from the culture by centrifugation or other operation may be used. Further, a product from treated cells of the microorganism may also be used. Specific examples of the product from treated cells include cells treated with acetone, toluene, etc.; disrupted cells; a cell free extract obtained from disrupted cells; and a crude or purified enzyme separated from cells. It is possible to recycle such cells or product after the reaction by using such cells or product after entrapping/immobilizing them in a cross-linked acrylamide gel or the like or immobilizing them in a solid carrier such as an ion exchange resin, diatom earth, etc. physically or chemically.

In the present invention, preferably, a malonic acid monoester may be prepared by the following procedures. Briefly, a cyanoacetic acid ester (a substrate) is added to a reaction medium to thereby dissolve or suspend the ester. A culture, etc. of the microorganism which will work as a catalyst is added to the reaction medium before or after the addition of the substrate. Then, a hydrolysis reaction is performed while controlling the reaction temperature and, if necessary, the pH of the reaction solution. As the reaction medium, deionized water or buffer may be used, for example. The reaction temperature is usually 0–70° C., preferably 10–35° C. A temperature at which the nitrilase activity of the microorganism cells, etc. is enhanced may be selected for the reaction. The pH of the reaction solution depends on the optimum pH of the enzyme of the microorganism used. Generally, it is preferable to perform the reaction at pH 6–9 because side-reactions resulting from the chemical hydrolysis can be inhibited at such pH levels. The concentration of the cells or product from treated cells in the reaction solution is usually 0.01 to 5% by weight in dry weight. The substrate concentration in the reaction solution is not particularly limited as long as it falls within the range from 0.01 to 70% by weight. Preferably, the substrate concentration is within the range from 0.1 to 15% by weight.

Further, it is possible to accumulate the malonic acid monoester at a high concentration by continuously adding the cyanoacetic acid ester during the hydrolysis reaction. At that time, in order to minimize the deactivation of the enzyme by the substrate, the substrate is added in such a manner that the substrate concentration in the reaction solution is maintained preferably at 0.01–10% by weight, more preferably at 0.1–5% by weight.

After completion of the reaction, the microorganism cells used as a catalyst are removed by centrifugation, filtration or the like. Then, it is possible to recover the unreacted cyanoacetic acid ester by extracting the resultant solution with a solvent such as hexane, ethyl acetate, etc. After the pH of the extraction residue is adjusted to 1–2 with an acid such as sulfuric acid, hydrochloric acid, etc., the residue is extracted with a solvent such as hexane, ethyl acetate, etc. to thereby obtain a malonic acid monoester, the reaction product.

BEST MODES FOR CARRYING OUT THE INVENTION

Hereinbelow, the present invention will be described more specifically with reference to the following Examples. However, the scope of the present invention is not limited to these Examples.

EXAMPLE 1

*Gordona terrae* MA-1 (FERM BP-4535) was inoculated into 3 ml of sterilized LB medium (1% polypeptone, 0.5% yeast extract, 0.5% NaCl) and cultured at 30° C. for 24 hrs under shaking. One milliliter of the resultant cell culture liquid was inoculated into 100 ml of the following sterilized medium A and cultured at 30° C. for 48 hrs.

| Medium A (pH 7.2) | |
|---|---|
| Glycerol | 1.0% |
| Isovaleronitrile | 0.2% |
| Yeast extract | 0.02% |
| $KH_2PO_4$ | 0.2% |
| NaCl | 0.1% |
| $MgSO_4 \cdot 7H_2O$ | 0.02% |
| $FeSO_4 \cdot 7H_2O$ | 10 ppm |
| $CoCl_2 \cdot 4H_2O$ | 10 ppm |
| $CaCl_2 \cdot 2H_2O$ | 1 ppm |
| $MnCl_2 \cdot 4H_2O$ | 7 ppm |

After completion of the cultivation, the culture liquid was centrifuged. The total volume of the resultant cells were washed with deionized water and then suspended in 100 ml of 50 mM phosphate buffer (pH 7.0). The turbidity of this cell suspension was $OD_{630}$=5.5. To this cell suspension, 1.00 g of ethyl cyanoacetate was added as a substrate and reacted at 30° C. for 1 hr. The resultant reaction solution was analyzed by high performance liquid chromatography (HPLC; column: TSKgel ODS-120A (Tosoh Corp.), 4.6 mm I.D.×25 cm; mobile phase: 5% acetonitrile, 95% water, 0.1% phosphoric acid; flow rate: 0.5 ml/min; detection: UV 220 nm). As a result, it was found that the whole substrate had been converted to monoethyl malonate. After completion of the reaction, cells were removed by centrifugation. Then, 2N HCl was added to the resultant solution to adjust the pH to 2.0. Thereafter, monoethyl malonate, the reaction product, was extracted from the solution with ethyl acetate. Anhydrous sodium sulfate was added to the resultant organic layer for dehydration, and the solvent was removed by distillation. As a result, 1.05 g of monoethyl malonate was obtained (yield: 89.9%).

EXAMPLE 2

Monoethyl malonate (1.07 g) was obtained (yield: 91.6%) in the same manner as in Example 1 except that *Corynebacterium nitrilophilus* ATCC 21419 was used as the microorganism.

EXAMPLE 3

Monomethyl malonate (0.97 g) was obtained (yield: 81.4%) in the same manner as in Example 1 except that methyl cyanoacetate was used as the substrate.

EXAMPLE 4

Mono-n-propyl malonate (1.05 g) was obtained (yield: 91.3%) in the same manner as in Example 1 except that n-propyl cyanoacetate was used as the substrate.

EXAMPLE 5

Monoisopropyl malonate (1.02 g) was obtained (yield: 88.7%) in the same manner as in Example 1 except that isopropyl cyanoacetate was used as the substrate.

EXAMPLE 6

Mono-n-butyl malonate (1.06 g) was obtained (yield: 93.4%) in the same manner as in Example 1 except that n-butyl cyanoacetate was used as the substrate. In the HPLC analysis, 40% acetonitrile, 60% water and 0.1% phosphoric acid were used as the mobile phase.

EXAMPLE 7

Mono-tert-butyl malonate (1.05 g) was obtained (yield: 92.5%) in the same manner as in Example 6 except that tert-butyl cyanoacetate was used as the substrate.

EXAMPLE 8

Monoallyl malonate (1.02 g) was obtained (yield: 87.2%) in the same manner as in Example 6 except that allyl cyanoacetate was used as the substrate.

EXAMPLE 9

Mono-2-ethylhexyl malonate (1.01 g) was obtained (yield: 91.8%) in the same manner as in Example 6 except that 2-ethylhexyl cyanoacetate was used as the substrate.

EXAMPLE 10

A reaction was performed in the same manner as in Example 6 except that benzyl cyanoacetate was used as the substrate. After completion of the enzyme reaction, 10% of the benzyl cyanoacetate was unreacted. The unreacted benzyl cyanoacetate was extracted with ethyl acetate for removal. After this extraction, 2N HCl was added to the resultant aqueous layer to adjust the pH to 2.0. Then, monobenzyl malonate, the reaction product, was extracted with ethyl acetate. Anhydrous sodium sulfate was added to the resultant organic layer for dehydration, and the solvent was removed by distillation. As a result, 0.89 g of monobenzyl malonate was obtained (yield: 80.3%).

EXAMPLE 11–19

To a cell suspension prepared in the same manner as in Example 1, ethyl cyanoacetate was added to give a concentration of 5–50% by weight and reacted at 25° C. for 20 hrs. After completion of the reaction, the yield was determined by liquid chromatography. The results are shown in Table 1.

TABLE 1

| Exa,mple | Substrate Concentration (% by weight) | Yield (%) |
| --- | --- | --- |
| 11 | 5 | 100 |
| 12 | 10 | 100 |
| 13 | 15 | 84.1 |
| 14 | 20 | 59.6 |
| 15 | 25 | 48.3 |
| 16 | 30 | 37.3 |
| 17 | 35 | 29.7 |
| 18 | 40 | 25.3 |
| 19 | 50 | 19.6 |

EXAMPLE 20

To 100 ml of a cell suspension prepared in the same manner as in Example 1, 5 g of ethyl cyanoacetate was added and reacted at 25° C. Thereafter, 30 g of ethyl cyanoacetate was further added to the reaction solution in portions while measuring the substrate concentration in the solution so that it did not exceed 5% by weight. After 30 hrs, the yield was 100%.

EXAMPLE 21

*Rhodococcus rhodochrous* ATCC 33025 was inoculated into 3 ml of sterilized LB medium (1% polypeptone, 0.5% yeast extract, 0.5% NaCl) and cultured at 30° C. for 24 hrs under shaking. One milliliter of the resultant cell culture liquid was inoculated into 100 ml of the following sterilized medium A and cultured at 30° C. for 48 hrs.

| Medium A (pH 7.2) | |
| --- | --- |
| Glycerol | 1.0% |
| Isovaleronitrile | 0.2% |
| Yeast extract | 0.02% |
| $KH_2PO_4$ | 0.2% |
| $MgSO_4 \cdot 7H_2O$ | 0.02% |
| $FeSO_4 \cdot 7H_2O$ | 10 ppm |
| $CoCl_2 \cdot 4H_2O$ | 10 ppm |
| $CaCl_3 \cdot 2H_2O$ | 1 ppm |
| $MnCl_2 \cdot 4H_2O$ | 7 ppm |

After completion of the cultivation, the culture liquid was centrifuged. The total volume of the resultant cells were washed with deionized water and then suspended in 100 ml of 50 mM phosphate buffer (pH 7.0). The turbidity of this cell suspension was $OD_{630}$=5.6. To this cell suspension, 1.00 g of n-propyl cyanoacetate was added as a substrate and reacted at 30° C. for 1 hr. The resultant reaction solution was analyzed by high performance liquid chromatography (HPLC; column: TSKgel ODS-120A (Tosoh Corp.), 4.6 mm I.D.×25 cm; mobile phase: 5% acetonitrile, 95% water, 0.1% phosphoric acid; flow rate: 0.5 ml/min; detection: UV 220 nm). As a result, it was found that the whole substrate had been converted to mono-n-propyl malonate. After completion of the reaction, cells were removed by centrifugation. Then, 2N HCl was added to the resultant solution to adjust the pH to 2.0. Thereafter, mono-n-propyl malonate, the reaction product, was extracted from the solution with ethyl acetate. Anhydrous sodium sulfate was added to the resultant organic layer for dehydration, and the solvent was removed by distillation. As a result, 1.06 g of mono-n-propyl malonate was obtained (yield: 89.9%).

EXAMPLE 22

Monoisopropyl malonate (1.01 g) was obtained (yield: 88.6%) in the same manner as in Example 21 except that isopropyl cyanoacetate was used as the substrate.

EXAMPLE 23

Mono-n-butyl malonate (1.05 g) was obtained (yield: 93.3%) in the same manner as in Example 21 except that n-butyl cyanoacetate was used as the substrate. In the HPLC analysis, 40% acetonitrile, 60% water and 0.1% phosphoric acid were used as the mobile phase.

EXAMPLE 24

Mono-tert-butyl malonate (1.04 g) was obtained (yield: 92.4%) in the same manner as in Example 23 except that tert-butyl cyanoacetate was used as the substrate.

EXAMPLE 25

Monoallyl malonate (1.04 g) was obtained (yield: 87.1%) in the same manner as in Example 23 except that allyl cyanoacetate was used as the substrate.

EXAMPLE 26

Mono-2-ethylhexyl malonate (1.00 g) was obtained (yield: 91.7%) in the same manner as in Example 23 except that 2-ethylhexyl cyanoacetate was used as the substrate.

EXAMPLE 27

A reaction was performed in the same manner as in Example 23 except that benzyl cyanoacetate was used as the substrate. After completion the enzyme reaction, 10% of the benzyl cyanoacetate was unreacted. The unreacted benzyl cyanoacetate was extracted with ethyl acetate for removal. After this extraction, 2N HCl was added to the resultant aqueous layer to adjust the pH to 2.0. Then, monobenzyl malonate, the reaction product, was extracted with ethyl acetate. Anhydrous sodium sulfate was added to the resultant organic layer for dehydration, and the solvent was removed by distillation. As a result, 0.88 g of monobenzyl malonate was obtained (yield: 80.2%).

EXAMPLE 28–36

To a cell suspension prepared in the same manner as in Example 21, n-propyl cyanoacetate was added to give a concentration of 5–50% by weight and reacted at 25° C. for 20 hrs. After completion of the reaction, the yield was determined by liquid chromatography. The results are shown in Table 2.

TABLE 2

| Example | Substrate Concentration (% by weight) | Yield (%) |
| --- | --- | --- |
| 28 | 5 | 100 |
| 29 | 10 | 100 |
| 30 | 15 | 85.1 |
| 31 | 20 | 57.6 |
| 32 | 25 | 44.3 |
| 33 | 30 | 32.3 |
| 34 | 35 | 26.7 |
| 35 | 40 | 20.3 |
| 36 | 50 | 15.6 |

EXAMPLE 37

To 100 ml of a cell suspension prepared in the same manner as in Example 21, 5 g of n-propyl cyanoacetate was added and reacted at 25° C. Thereafter, 20 g of n-propyl cyanoacetate was further added to the reaction solution in portions while measuring the substrate concentration in the solution so that it did not exceed 5% by weight. After 30 hrs, the yield was 100%.

INDUSTRIAL APPLICABILITY

According to the present invention, it is possible to prepare malonic acid monoesters useful as intermediates in the synthesis of various chemical products, medicines, agricultural chemicals and the like with high productivity.

What is claimed is:

1. A method for preparing a malonic acid monoester represented by formula (II):

HOOC—CH$_2$—COOR  (II)

wherein R is alkenyl, aryl, non-substituted aralkyl or C$_{1\text{-}20}$ alkyl, comprising treating a cyanoacetic acid ester represented by formula (I):

NC—CH$_2$—COOR  (I)

wherein R is as defined above,
with a culture, cells or a product from treated cells of a microorganism belonging to the genus Corynebacterium, Gordona or Rhodococcus and having nitrilase activity, to hydrolyze said cyanoacetic acid ester.

2. The method according to claim 1, wherein said cyanoacetic acid ester is continuously added to the reaction solution while maintaining the concentration of said cyanoacetic acid ester in said solution in the range from 0.01 to 10% by weight during the hydrolysis.

3. The method according to claim 1, wherein said C$_{1\text{-}20}$ alkyl represented by R is C$_{3\text{-}20}$ alkyl and said microorganism having nitrilase activity is a microorganism belonging to the genus Rhodococcus.

4. The method according to claim 3, wherein said cyanoacetic acid ester is continuously added to the reaction solution while maintaining the concentration of said cyanoacetic acid ester in said solution in the range from 0.01 to 10% by weight during the hydrolysis.

5. The method according to claim 1, wherein said microorganism having nitrilase activity is *Corynebacterium nitrilophilus* ATCC 21419.

6. The method according to claim 1 wherein said microorganism having nitrilase activity is *Gordona terrae* MA-1 (FERM BP-4535).

7. The method according to claim 1, wherein said microorganism having nitrilase activity is *Rhodococcus rhodochrous* ATCC 33025.

8. A method for preparing a malonic acid monoester represented by formula (II'):

HOOC—CH$_2$—COOR'  (II')

wherein R' is alkenyl, aryl, non-substituted aralkyl or C$_{3\text{-}20}$ alkyl,
comprising treating a cyanoacetic acid ester represented by formula (I'):

NC—CH$_2$—COOR'  (I')

wherein R' is as defined above,
with a culture, cells or a product from treated cells of a microorganism having nitrilase activity, to hydrolyze said cyanoacetic acid ester.

9. The method according to claim 8, wherein said cyanoacetic acid ester is continuously added to the reaction solution while maintaining the concentration of said cyanoacetic acid ester in said solution in the range from 0.01 to 10% by weight during the hydrolysis.

10. The method according to claim 1, wherein the non-substituted aralkyl represented by R is benzyl.

11. The method according to claim 8, wherein the non-substituted aralkyl represented by R' is benzyl.

* * * * *